United States Patent [19]

Kamrat

[11] Patent Number: 4,776,697
[45] Date of Patent: Oct. 11, 1988

[54] METHOD FOR THE ILLUMINATION OF PARTICLES CONTAINED IN A MEDIUM FOR AN OPTICAL ANALYSIS, AND AN OPTICAL PARTICLE ANALYSER

[75] Inventor: Esko Kamrat, Vantaa, Finland
[73] Assignee: K-Patents Oy, Helsinki, Finland
[21] Appl. No.: 532
[22] Filed: Jan. 5, 1987

[30] Foreign Application Priority Data

Jan. 8, 1986 [FI] Finland .................................. 860075

[51] Int. Cl.$^4$ .......................................... G01N 21/49
[52] U.S. Cl. .................................. 356/336; 356/339; 356/244
[58] Field of Search ................. 356/38, 335, 336, 337, 356/338, 339, 244; 250/574

[56] References Cited

U.S. PATENT DOCUMENTS 3,564,262  2/1971  Hach .................................... 250/218
3,975,084  8/1976  Block .................................... 356/103

Primary Examiner—Davis L. Willis
Assistant Examiner—Matthew W. Koren

[57] ABSTRACT

The invention relates to a method for the illumination of particles contained in a medium for an optical analysis, and to an optical particle analyser. The medium (1) thereby makes contact with a window (2), and a light beam illuminating the particles is directed into the medium through the window in order to form an image of the particles. In order to enable an accurate quantitative and qualitative analysis carried out directly from the medium, the light beam is modified into a beam (5) having a predetermined thickness in the direction of the normal of the window. The beam (5) is directed to advance in the medium containing the particles close to and substantially in parallel with a window surface (6) making contact with the medium in order to illuminate particles (10) contained in a predetermined volume part (9) of the medium for the formation of an optical image (8).

4 Claims, 1 Drawing Sheet

METHOD FOR THE ILLUMINATION OF PARTICLES CONTAINED IN A MEDIUM FOR AN OPTICAL ANALYSIS, AND AN OPTICAL PARTICLE ANALYSER

FIELD OF THE INVENTION

The invention relates to a method for the illumination of particles contained in a medium for an optical analysis, wherein the medium is in contact with a window, and a light beam illuminating the particles is directed to the medium through the window in order to form an image of the particles, and the light beam is modified into a beam having a predetermined thickness in the direction of the normal of the window, and the light beam is directed to advance in the medium containing particles close to and substantially in parallel with a window surface making contact with the medium so as to illuminate particles contained in an accurately predetermined volume part of the medium. The invention is also concerned with a particle analyser utilizing said method.

BACKGROUND ART

This kind of methods for the illumination of particles as well as the analysers utilizing such methods are widely known in industrial use. Today it is customary in the industries to transport or treat a material in the form of a particle suspension in a medium, such as a liquid. The particle may thereby be e.g. a crystal, fibre, grain, bubble, droplet, etc. The medium may be e.g. water or a suitable gaseous substance.

The observation and control of different kinds of manufacturing processes requires data on the amount, size distribution or shape of particles. It is of advantage if such data can be obtained quickly and continuously. Therefore, it is selfevident that the best way of obtaining the data would be to use an analyser which measures directly from a process pipe or a container. This would guarantee that the measured sample gives reliable information on the process.

According to the principle of optical measurement, particles are illuminated in a particle analyser, and the light reflected by the particles is measured by means of an optical detector. The choice of the optical detector depends on the analysis to be carried out in each particular case. The optical detector may thus be of any type, beginning from a simple photocell up to a multi-element image analyser. The reflected light can also be examined with the naked eye or by means of suitable auxiliary optics. Essential is that the illlumination of the particles is so arranged that the illuminated volume part of the medium is accurately defined and known. When only the particles contained in a determined volume part are illuminated, a good contrast is obtained for the image received by the optical detector. As to quantitative analysis, a decisive advantage is obtained when the liquid volume in which the illuminated particles are contained is known.

Amongst previous solutions may be mentioned a crystal microscope widely used in the sugar industries, e.g. Jungner Crystal Projector type KP3. This device comprises two windows between which the suspensions to be measured is passed. The windows form two mutually spaced parallel planar surfaces the spacing of which is adjustable. Particles, e.g. sugar crystals, are illuminated through one window, and the image of the particles is formed by means of an objective positioned behind the other window. The image is projected on a matt-finished glass plate on an enlarged scale so that the operators are able to observe the size and the shape of the particles. The contrast is poor, because the illuminated particles are seen against the light, so that no accurate electronic automated image analysis is possible. No quantitative conclusions, either, can be drawn, because the flow in the slit defined between the windows does not provide reliable information on the main flow, i.e. the sample is not representative enough.

Another very large group of known devices consists of so-called photometers which measure the absorption or the reflection of light caused by the particles. A typical example of photometers is the device disclosed in U.S. Pat. No. 3,962,581. It is characteristic of a device of the photometer type that the illumination is formed by a cone of rays passed substantially perpendicularly through the process window. One drawback is that the illuminated volume part is not accurately defined, do that the device can be used only for a quantitative determination based on an adjustement curve. The adjustment curve has to be determined experimentally separately for each application.

Another known photometer-type solution is the so-called Total Power method, which is part of the Nordmiljö 80 project. By means of this solution it is possible to obtain some qualitative information, too; mainly concerning the fibre length distribution. In the device applying the solution, the suspension flows within a glass tube and the device is used for measuring the average value and the time distribution of the light reflected by the particles. The ratio of the distribution and the average value serves as a kind of measure for the particle size. This solution, too, has the disadvantage that it cannot be used for a determination carried out directly from a process, because the sample flows in a small measuring cuvette. Accordingly, the representativeness of the sample is questionable.

SUMMARY OF THE INVENTION

The object of the invention is to provide a method and a device for applying said method, by means of which the above drawbacks can be obviated. This is achieved by means of a method according to the invention which is characterized in that the window is a trapezoidal prism the longer one of the parallel side surfaces of which forms the surface making contact with the medium, and that the light beam is directed to be passed through one oblique surface of the prism. The device according to the invention, in turn, is characterized in that the window is a trapezoidal prism the longer one of the parallel side surfaces of which forms the window surface making contact with the medium, and that the light beam is directed to be passed through one oblique surface of the prism.

The invention is advantageous in that it provides an analyser by means of which an accurate quantitative and qualitative analysis of the particles can be carried out directly from a main flow. The illuminated volume part is extremely accurately defined and easily adjustable. The contrast of the optical image reflected by the particles is good, because the particles are seen against an unilluminated background. A further advantage is that it is possible to obtain additional information by observing the decrease in the illumination of the particles in the direction of the movement of the light. With regard to the quantitative analysis, it is advantageous that the method can be used for measuring the movement of the particles, by virtue of which the speed of the particles and, further, the flow rate of the medium can be determined.

BRIEF DESCRIPTION OF THE DRAWING

The invention will be described in the following in more detail by means of one preferred embodiment of the invention shown in the attached drawings, wherein.

DESCRIPTION OF THE PREFERRED EMBODIMENTS

Figure 1:
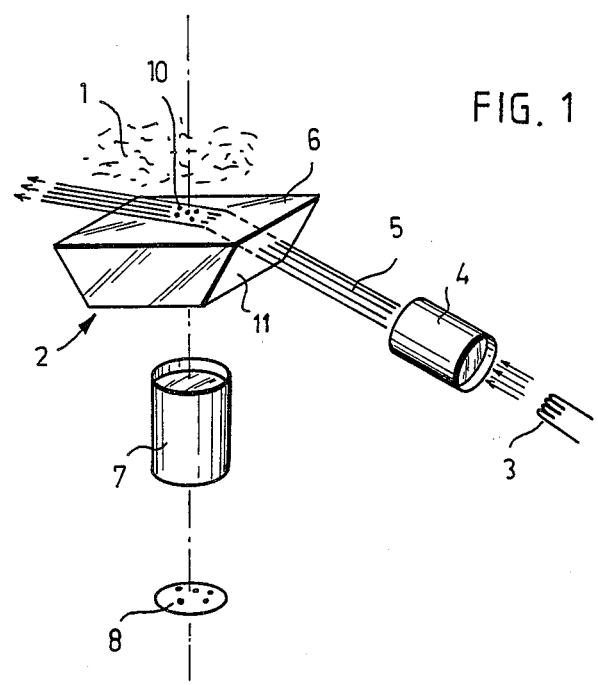
FIG. 1 is a general view of the structure and the operation of a device according to the invention.

FIG. 1 illustrates generally the structure and the operating principle of the device according to the invention. A particle suspension flow 1 consisting of a medium and particles contained therein, and an optical system provided for measuring this flow are separated from each other by means of a window 2. Accordingly, the particle suspension flows in FIG. 1 over the upper surface of the window 2, so that the upper surface of the window 2 makes contact with the particle suspension.

A light source is indicated in FIG. 1 by means of the reference numeral 3. A beam of light from the light source 3 is modified by means of condenser optics 4 in the direction of the normal of the window into a ribbon-like beam 5 having an accurately predetermined thickness. According to the invention, this ribbon-like beam of light is directed so that it advances in the medium containing particles close to and substantially in parallel with a window surface 6 making contact with the medium, i.e. with the suspension containing particles. The expression "substantially in parallel" here means that the angle between the ribbon-like beam 5 and the surface 6 is small. In addition, the beam and the surface are close to each other.

Figure 2:
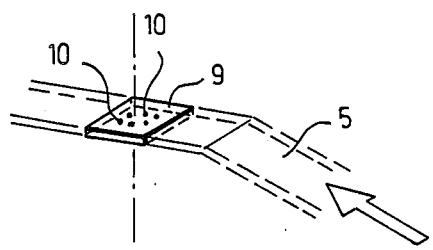
FIG. 2 is a general view of an accurately defined illuminated volume part.

When the thickness of the light beam 5 is accurately determined and the beam advances close to the surface 6 and substantially in parallel therewith, particles 10 contained in an accurately predetermined volume part 9 of the medium flow are illuminated. This accurately determined volume part 9 is shown in FIG. 2. The illuminated particles 10, in turn, are illustrated generally in FIGS. 1 and 2. The direction of the movement of the light beam 5 is shown by means of arrows in FIG. 2.

The image of the particles 10 illuminated as described above is projected by means of an objective lens system 7, and an image 8 is formed on an image plane, and this image can be analysed with the naked eye or it can be modified into a signal by means of a detector.

The window cannot be formed by a normal window having parallel planar surface, because a beam of light coming from the air through one planar surface into the window material bends within the material towards the surface normal, with the result that the angle between the surface in contact with the medium and the light beam passed into the medium through the surface is too wide.

The window can be e.g. a trapezoidal prism. In the example of the figures the prism is so positioned that the longer one of the parallel side surfaces thereof forms the surface 6. The ribbon-like light beam 5 is thereby directed to pass through one oblique surface 11 of the prism. Since the material of the prism is optically denser than the medium, the beam 5 bends in a direction away from the surface normal. By giving the beam 5 the proper angle of incidence, the ribbon-like beam 5 and the surface 6 are made substantially parallel and positioned close to each other. The illuminated volume part 9 is adjusted in the direction of the normal of the surface 6 by providing the condenser optics 4 with limiters which accurately adjust the thickness of the beam 5 to the desired value. In the plane of the surface 6 the defining of the volume part 9 can be effected e.g. by means of a limiter of the visual field of the objective 7.

The embodiment described above is by no means intended to restrict the invention, but the invention can be modified within the scope of the claims in various ways. Accordingly, the device according to the invention or the parts thereof do not need to be exactly similar to those shown in the figures, but other solutions can be used as well. The window 2 can also be formed of a prism of some other shape, so that e.g. the internal reflection of the prism can be utilized. Thereby the direction of incidence and the point of incidence of the light beam have to be chosen so that the beam advances within the medium substantially in parallel with and close to the surface making contact with the medium. Even though the above example relates to the analysis of a flowing particle suspension, it is self-evident that the method and the device can also be used for the analysis of a non-flowing suspension. Further, the light beam does not need to be ribbon-like, but other kinds of beams are possible as well.

What is claimed is:

1. A method for the illumination of particles contained in a medium for an optical analysis, wherein the medium is in contact with a window, and a light beam illuminating the particles is directed to the medium through the window in order to form an image of the particles, and the light beam is modified into a beam having a predetermined thickness in the direction of the normal of the window, and the light beam is directed to advance in the medium containing particles close to and substantially in parallel with a window surface making contact with the medium so as to illuminate particles contained in an accurately predetermined volume part of the medium, wherein the window is a trapezoidal prism the longer one of the parallel side surfaces of which forms the surface making contact with the medium, and that the light beam is directed to be passed through one oblique surface of the prism.

2. A method according to claim 1, wherein an image is formed of the light reflected back from the particles through the window.

3. An optical particle analyzer, comprising a window arranged to be in contact with a medium containing particles to be analyzed, a light source arranged to illuminate the particles through the window, and a lens system arranged to form an optical image of the illuminated particles, the device comprising an optical means arranged to modify a light beam from the light source into a ribbon-like beam having an accurately predetermined thickness, and the ribbon-like light beam is directed to advance in the medium containing particles close to and substantially in parallel with a window surface making contact with the medium, wherein the window is a trapezoidal prism the longer one of the parallel side surfaces of which forms the window surface making contact with the medium, and that the light beam is directed to be passed through one oblique surface of the prism.

4. A particle analyzer according to claim 3, wherein the lens system is arranged to gather the light reflected back from the particles contained in an accurately determined volume part of the medium flow and illuminated by the ribbon-like light beam, in order to form an optical image.

* * * * *